United States Patent [19]
Jaquiss et al.

[11] 4,188,496
[45] Feb. 12, 1980

[54] PROCESS FOR PREPARING 2,2-BIS(4-HYDROXY-PHENYL) PROPANE FROM DISTILLATION BY-PRODUCTS THEREOF

[75] Inventors: Donald B. G. Jaquiss, New Harmony; Lawrence C. Mitchell, Mt. Vernon, both of Ind.

[73] Assignee: General Electric Company, Pittsfield, Mass.

[21] Appl. No.: 863,667

[22] Filed: Dec. 23, 1977

[51] Int. Cl.$^2$ .................. C07C 37/44; C07C 37/24
[52] U.S. Cl. ................................ 568/723; 568/724; 568/728
[58] Field of Search .................... 568/724, 728, 723

[56] References Cited
U.S. PATENT DOCUMENTS

| | | | |
|---|---|---|---|
| 3,073,868 | 1/1963 | Prahl et al. | 260/619 |
| 3,221,061 | 11/1965 | Grover et al. | 568/728 |
| 3,290,390 | 12/1966 | Prahl et al. | 568/728 |
| 3,290,391 | 12/1966 | Prahl et al. | 260/619 |
| 3,326,986 | 6/1967 | Dugan et al. | 260/619 |
| 3,673,262 | 6/1972 | Prahl et al. | 260/619 A |
| 3,919,330 | 11/1975 | Kwantis et al. | 260/619 R |
| 3,972,950 | 8/1976 | Kwantis | 260/619 A |

FOREIGN PATENT DOCUMENTS

| | | |
|---|---|---|
| 1294664 | 5/1969 | Fed. Rep. of Germany . |
| 54374 | 3/1967 | German Democratic Rep. . |
| 6617478 | 2/1960 | Japan . |
| 1149322 | 4/1969 | United Kingdom . |

OTHER PUBLICATIONS

Hirt et al., "Chem. Ab.", 67:53879h (1967).
Kunoshimo Chemical Ltd., "Chem. Ab.", 66:38331; (1967).

Primary Examiner—Norman Morgenstern
Attorney, Agent, or Firm—Morgan, Finnegan, Pine, Foley & Lee

[57] ABSTRACT

A process is disclosed for the production of 2,2-bis(4-hydroxyphenyl) propane, herein referred to as bisphenol-A, from by-products remaining after purification distillation of bisphenol-A produced from a condensation reaction of phenol and acetone. The process comprises mixing the by-products with phenol and treating the resulting mixture with anhydrous hydrogen bromide to isomerize those by-products isomerizable to bisphenol-A for subsequent recovery.

6 Claims, No Drawings

PROCESS FOR PREPARING 2,2-BIS(4-HYDROXY-PHENYL) PROPANE FROM DISTILLATION BY-PRODUCTS THEREOF

This invention concerns a process using anhydrous hydrogen bromide to produce 2,2-bis(4-hydroxyphenyl)propane from by-products remaining after purification distillation of 2,2-bis(4-hydroxyphenyl)propane produced from a condensation reaction of phenol and acetone.

BACKGROUND OF THE INVENTION

The use of high purity 2,2-bis(4-hydroxyphenyl)propane, herein referred to as bisphenol-A, as a reactant in the preparation of subsequent formulations such as the preparation of polycarbonate resins is well known in the art. One method for obtaining bisphenol-A of the purity needed is to distill crude bisphenol-A. In such distillations, various by-products remain and these primarily include higher condensation products of bisphenol-A, condensation products of phenol and acetone produced in the original bisphenol-A formation, colored substances, isomers of bisphenol-A, and the like. Prahl et al, U.S. Pat. No. 3,290,390, disclose the addition of phenol to the by-products and contacting the resulting mixture with an acidic agent such as hydrogen chloride at between room temperature and 150° C. to produce therefrom bisphenol-A. However, the method of Prahl et al requires, according to their examples, 16 hours or more reaction time.

It has now been discovered that it is possible to convert such by-products isomerizable to bisphenol-A to said bisphenol-A in a vastly shorter period of time by treating a mixture of the by-products and phenol with anhydrous hydrogen bromide. The process of this invention yields bisphenol-A in solution for a subsequent recovery such as by cooling to produce a 1:1 bisphenol-A/phenol adduct, from which the bisphenol-A can then be recovered, by procedures known per se.

In practice, commercial plants utilize distillation of bisphenol-A as a step in the purification process. The bottoms from the distillation are called "tars" and conventionally these are disposed of by burning. This represents a serious loss in yield because tars contain from 20–60% bisphenol-A plus the isomerizable by-products mentioned above. Experiments have shown that the amount of bisphenol-A in a typical tar can be increased from 30% to 60% by isomerization with anhydrous HBr and more than half of this bisphenol-A can be recovered, e.g., by crystallization. The mother liquor from the crystallization can be stripped of phenol (for recycle) in a separate column, and the diminished quantity of "tar" remaining can be burned or otherwise utilized.

DESCRIPTION OF THE INVENTION

According to the present invention, there is provided a process for the production of 2,2-bis(4-hydroxyphenyl)propane from by-products which contain products isomerizable to 2,2-bis(4-hydroxyphenyl)propane and which remain after purification distillation of 2,2-bis(4-hydroxyphenyl)propane produced by the condensation of phenol and acetone, said process comprising (i) preparing a starting mixture of by-products and phenol, said by-products containing products isomerizable to 2,2-bis(4-hydroxyphenyl)propane;

(ii) adding anhydrous hydrogen bromide to the starting mixture and isomerizing said by-products to 2,2-bis(4-hydroxyphenyl)propane; and (iii) subsequently recovering said 2,2-bis(4-hydroxyphenyl)propane.

The by-products contemplated herein are generally referred to as waste streams in commercial purification of bisphenol-A and are many times merely disposed of without treatment to reclaim additional bisphenol-A. In general, the by-products are (1) tar by-products defined as higher condensation products of bisphenol-A which are bisphenol-A molecules coupled with themselves and which remain as residue in the purification distillation of bisphenol-A, and (2) isomer by-products, defined as products of phenol and acetone removed with the bisphenol-A fraction during said purification distillation. The by-products further include colored substances and various other unknowns.

Obviously, not all components of these by-products are viable candidates for conversion to bisphenol-A. However, it has now been discovered that within a relatively short period of time additional bisphenol-A can be claimed from these by-products by mixing said by-products with phenol and treating the resulting mixture with anhydrous hydrogen bromide. The ratio of phenol to by-product which creates a preferred mixture is about 1–1.5:1 by weight. The hydrogen bromide must be thoroughly mixed with the phenol and by-product reactants.

Copending application Ser. No. 863,666, filed on even date with this application and assigned to the same assignee, discloses a process to produce 2,2-bis(4-hydroxyphenyl)propane from such by-products by using anhydrous hydrogen chloride under superatmospheric pressure. Use of superatmospheric pressure substantially reduces the reaction time required. Likewise, the use of anhydrous hydrogen bromide disclosed herein also substantially reduces the reaction time required, but does so without utilization of superatmospheric pressure, requiring only ambient pressure for utility.

Recovery of the bisphenol-A thus produced can be accomplished by various procedures as known in the art. In one such procedure the hydrogen bromide is first stripped from the mixture, and then the mixture is allowed to cool to a temperature where an essentially equimolar adduct of bisphenol-A/phenol adduct crystallizes. Said adduct can be mechanically removed as by filtration or centrifugation from the remaining components and the bisphenol-A separated therefrom.

DESCRIPTION OF A PREFERRED EMBODIMENT

The following example is set forth to illustrate more clearly the principle and practice of this invention to those skilled in the art. Unless otherwise specified, where parts or percents are mentioned, they are parts or percents by weight.

EXAMPLE

From a mixture of 1,024 grams of phenol and 990 grams of tar by-products from a phenol-acetone condensation reaction, 385.6 grams are taken and charged to a 500 ml flask equipped with a stirrer, thermometer, and condenser. The ratio of phenol to by-product tar is therefore 1.03:1. Analysis by gas chromatography shows that this starting mixture contains 14% bisphenol-A. The starting temperature is 34° C., and no temperature control of the reaction is exercised. A total of 16 grams of anhydrous HBr is added to the mixture at the rate of 1 gram per minute and the mixture is continuously stirred throughout the 16 minute period. The hydrogen bromide metered addition is accomplished at ambient pressure through utilization of a dip tube as known in the art. At the end of hydrogen bromide addition (16 minutes), the temperature of the reaction has risen to 52° C.

Analysis by gas chromatography of the completed reaction mix for bisphenol-A content shows 29.4% bisphenol-A in the mix, 2.10 times the amount of the bisphenol-A present in the starting mixture.

Upon cooling and reheating to 45° C., the reaction mixture remains viscous. Two hundred grams of 45° C. phenol are added and, upon stirring, the temperature rises to 50° C. The temperature is then lowered to 33° C. for formation of a 1:1 bisphenol-A/phenol molar adduct. Results of gas chromatographic analysis of the adduct thus formed shows 49% of the bisphenol-A present in the completed reaction mix is present in the adduct formed.

Thus, in a period of only 16 minutes and at ambient pressure, a yield of more than twice as much of the bisphenol-A present in the starting mixture is attained in the completed reaction mix, exemplifying the isomerization of certain components of the by-products to bisphenol-A.

Obviously, other modifications and variations of the present invention are possible in light of the above teachings. It is, therefore, to be understood that changes may be made in the particular embodiments of the invention described which are within the full intended scope of the invention as defined by the appended claims.

We claim:
1. A process for the production of 2,2-bis(4-hydroxyphenyl)propane from by-products which contain products isomerizable to 2,2-bis(4-hydroxyphenyl)propane and which remain after purification distillation of 2,2-bis(4-hydroxyphenyl)propane produced by the condensation of phenol and acetone, said process comprising
   (i) preparing a starting mixture of by-products and phenol, said by-products containing products isomerizable to 2,2-bis(4-hydroxyphenyl)propane;
   (ii) adding anhydrous hydrogen bromide to the starting mixture and isomerizing said by-products to 2,2-bis(4-hydroxyphenyl)propane at ambient pressure; and
   (iii) subsequently recovering said 2,2-bis(4-hydroxyphenyl)propane.

2. A process as defined in claim 1 wherein the products isomerizable to 2,2-bis(4-hydroxyphenyl)propane are higher condensation products of bisphenol-A.

3. A process as defined in claim 1 wherein the products isomerizable to 2,2-bis(4-hydroxyphenyl)propane are condensation products of phenol and acetone.

4. A process as defined in claim 1 wherein the by-products and phenol in the starting mixture are essentially equal in weight.

5. A process as defined in claim 1 wherein the addition of anhydrous hydrogen bromide is continuous throughout the time of reaction.

6. A process as defined in claim 1 wherein about 4% by weight of anhydrous hydrogen bromide is added to the starting mixture.

* * * * *